United States Patent
Fischer et al.

[11] Patent Number: 6,155,825
[45] Date of Patent: Dec. 5, 2000

[54] RADIOPAQUE ENDODONTIC MARKING TOOLS AND RELATED METHODS

[75] Inventors: Dan E. Fischer, Sandy; Dan J. Bills, West Jordan, both of Utah

[73] Assignee: Ultradent Products, Inc., South Jordan, Utah

[21] Appl. No.: 09/356,636

[22] Filed: Jul. 19, 1999

[51] Int. Cl.[7] .................................................. A61C 5/02
[52] U.S. Cl. ................................................................ 433/102
[58] Field of Search ........................ 433/102, 224, 433/165, 166, 81

[56] References Cited

U.S. PATENT DOCUMENTS

| | | | |
|---|---|---|---|
| 3,330,040 | 7/1967 | Kahn | 433/224 |
| 3,772,791 | 11/1973 | Malmin | 433/224 |
| 4,190,958 | 3/1980 | Martin et al. | 433/102 |
| 4,265,618 | 5/1981 | Herskovitz et al. | 433/32 |
| 4,337,038 | 6/1982 | Saito et al. | 433/32 |
| 4,571,180 | 2/1986 | Kulick | 433/72 |
| 4,684,346 | 8/1987 | Martin | 433/166 |
| 4,738,620 | 4/1988 | Tomasini | 433/72 |
| 5,154,611 | 10/1992 | Chen | 433/77 |
| 5,320,529 | 6/1994 | Pompa | 433/76 |
| 5,464,362 | 11/1995 | Heath et al. | 451/48 |
| 5,538,424 | 7/1996 | Gelb | 433/72 |
| 5,558,652 | 9/1996 | Henke | 604/280 |
| 5,807,106 | 9/1998 | Heath | 433/102 |

*Primary Examiner*—John J. Wilson
*Assistant Examiner*—Melba Bumgarner
*Attorney, Agent, or Firm*—Workman Nydegger & Seeley

[57] ABSTRACT

Enhanced radiographic detection is provided by an endodontic marking instrument having a high density radiopaque elongate member, thereby enabling a dentist to better identify the location of the instrument in a root canal and the length of the root canal. The high density, high contrast material of the elongate member is a non-toxic, high density, radiopaque, metallic material such as gold, platinum, palladium, silver, tungsten, and the like. The endodontic marking tools of the present invention are distinctly visible on radiographic images in light of the substantial contrast between the high density radiopaque material and the tooth of the patient.

8 Claims, 3 Drawing Sheets

RADIOPAQUE ENDODONTIC MARKING TOOLS AND RELATED METHODS

BACKGROUND OF THE INVENTION

1. The Field of the Invention

This invention is in the field of instruments for use in medicine and dentistry. More specifically, this invention is in the field of endodontic instruments for treating root canals as part of a root canal procedure.

2. The Relevant Technology

To preserve a tooth that has a diseased pulp cavity, it is necessary to prevent bacterial proliferation within the pulp canal of the tooth by removing the diseased or necrotic pulp material from the pulp canal. After the pulp material has been removed or extirpated from a tooth, the pulp cavity is typically filled or obturated with a material such as gutta percha to occlude the pulp cavity and a sealer to seal the pulp cavity. This procedure is referred to as root canal therapy. Root canal cleaning is generally achieved by hand or mechanical instrumentation with files that are configured to bore and cut.

It is also common during the root canal procedure to irrigate a pulp cavity and the various root canals involved using an endodontic irrigator tip. Irrigation assists in removing debris and necrotic material cut by the endodontic files and bores. Disinfecting solutions can also be employed in irrigation, thereby disinfecting the pulp cavity and root canals during the operative procedure.

Root canals are often thin, tight, twisted and cumbersome to negotiate. A major problem associated with negotiating such awkward spaces during root canal therapy is apical perforation, i.e., perforation of the apex of the root canal. Another problem involves failing to clean material close enough to the apex, thus leaving necrotic tissue within the root canal. Before instrumentation of a root canal, the length of the root canal is determined to identify a suitable working length for the file or irrigation tip. Generally, the working length corresponds to the distance from a fixed reference position on the crown of a tooth to the apex.

Radiography is the most common method for measuring the length of the root canal. A preoperative x-ray image of the diseased tooth is taken from the front or back of the tooth, as depicted in FIG. 1, to show a cross-sectional view of the root canals 12 of tooth 10. The length of the root canal and the desired working length of the file or irrigation tip to be placed therein are then estimated.

Apical perforations typically result from an error in estimating the length of a root canal or the working length of the file or irrigation tip. Perforation of the apex 14 of a root canal 12 can result from the use of files or endodontic irrigation tips which are too long. Similarly, apex 14 can be perforated by extrusion of infected material through the apex due to the force exerted by the file or tip on the material as the file or tip is pushed downward to reach the apex. In addition to exposing the tissue surrounding the tooth to the infected material, apical perforations also substantially complicate subsequent healing of the root canal.

The possibility of perforating the apex is particularly frustrating because it is often desirable to deliver fluid which reaches the apex in order to disinfect the apex and dissolve necrotic tissue therein. However, certain fluids are too viscous to reach the apex if delivered too far above the apex or may entrap air, which prevents the fluid from reaching the apex.

Incomplete removal of necrotic material can thus result from the failure of a dental tool to reach far enough into a root canal. In light of the desire to maneuver dental tools close to the apex without perforating the apex, practitioners have followed up the initial radiographic procedure described above by placing a radiopaque instrument into the root canal of an opened tooth, then making a radiographic image of the root canal with the radiopaque instrument disposed therein, e.g., by taking an x-ray. This follow up procedure radiographically records the position of the tip of the instrument with respect to the apex of the root canal. Based on the x-ray with the tool in the root canal, the practitioner is able to adjust the penetrating length of a file or other tool.

The radiographic tools of the prior art have typically been the cutting tools, e.g., files, employed by the dentist during cleaning of the root canal. However, such typical cutting tools, particularly the smaller diameter tools, often yield a low contrast between the tools and the tooth in which the tools have been placed. Such radiographic tools are typically extremely thin, having a circumference measuring in the thousandths of inches in some circumstances. Consequently, it is often very difficult to clearly see and determine apex proximity of such typical radiographic tools on an x-ray image. Such low contrast tools typically comprise, for example, stainless steel or nickel-titanium as the radiographic material. Sonic techniques and electrical convective techniques can also be used in addition to radiographic techniques, but they are not always entirely accurate.

There is therefore a need within the art for an improved endodontic marking instrument and a method for using the instrument.

SUMMARY AND OBJECTS OF THE INVENTION

It is therefore an object of the invention to provide an improved endodontic tool and methods for making and using the tool.

It is another object of the invention to provide an improved endodontic marker.

It is another object of the invention to provide an endodontic marking tool which comprises a radiographic material having a high degree of contrast from the tooth of a patient.

In order to achieve the foregoing objects of the invention, endodontic marking tools comprising a high density radiopaque material are provided. The high density material is a non-toxic, high contrast, radiopaque, metallic material. The endodontic marking tools of the present invention show up significantly more clearly on radiographic images in light of the substantial contrast between the high density radiopaque material and the tooth of the patient. The radiopaque endodontic marking tools of the present invention are configured for placement within a root canal for detection by a radiographic instrument, such as an x-ray machine.

By way of example, the high density material employed in the tools of the present invention may include a high density material selected from the group consisting of gold, platinum, palladium, silver, and tungsten. Other embodiments further include an alloying agent.

A tool of the present invention comprises an elongate member having a distal insertion end and a proximal end. The elongate member has sufficient rigidity and ductility to be placed within and negotiate the angles of a root canal of a tooth such that the elongate member can be extended to a desired location within the root canal. The elongate member has a length and outer diameter that permits insertion of the elongate member into a root canal of a tooth.

By way of example, the endodontic tool may be an endodontic file, a slender rod or wire, a bit, or a variety of other tools which will permit insertion within a root canal. The shape of the tool may be cylindrical, tapered, or a variety of configurations. The endodontic tool may be used solely as a radiopaque marker, or may also optionally be employed as a cutting tool, or other tool, prior to or following radiography.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 2:
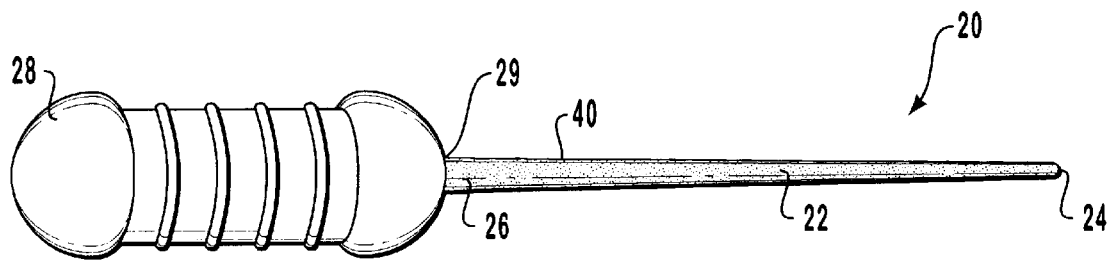
FIG. 2 is a top view of one embodiment of an endodontic marking tool of the present invention.

With reference now to FIG. 2, an endodontic marking tool 20 of the present invention is shown. Tool 20 comprises a high density, high contrast, radiopaque material. As used throughout this specification and the appended claims, the phrase "high density material" refers to a material having an atomic number of 29 or higher, preferably 37 or higher. The endodontic marking tools of the present invention show up significantly more clearly on radiographic images in light of the substantial contrast between the high density radiopaque material of the tools and the tooth of the patient.

Tool 20 comprises an elongate member 22 having a distal insertion end 24 and a proximal end 26. A handle 28 partially ensheathes elongate member 22.

The features of high density and improved radiopacity are important features of member 22. In addition, member 22 comprises a non-toxic material. Thus, member 22 may be placed in the mouth of a patient. Since member 22 will likely encounter blood, saliva, water, endodontic pulp material and other fluid and cellular material, and should be sterile when used, the material employed in member 22 is preferably autoclavable, corrosion resistant, and oxidation resistant. However, a disposable embodiment is also available.

Member 22 is also rigid enough to be extended into a root canal, yet ductile or pliant enough to negotiate root canal areas. Furthermore, member 22 is configured with a length and outer diameter that permits insertion of elongate member 22 into a root canal of a tooth. The desired material for member 22 also has physical properties conducive to being formed into tools which permit insertion, yet negotiate the parameters of the root canal without breaking.

Examples of materials which can be employed as high density materials include gold, platinum, palladium, silver, tungsten, and the like, each of which are nontoxic, capable of being formed into tools which permit insertion, and in light of their high density are useful within the oral cavity as radiopaque markers. These materials have a high contrast when exposed to x-rays or other radiographic equipment. The resulting radiographic images show much higher contrast between the endodontic marking tool and the patient's tooth. This feature is of particular importance since the typical endodontic tools used often have a very small diameter, i.e., in the thousandths of inches in certain circumstances.

Gold, platinum, and palladium are autoclavable, corrosion resistant, and oxidation resistant. These materials can be employed in pure form for member 22 or in alloy form, e.g., to increase hardness. Thus, in one embodiment, member 22 is formed from a pure, high density material. In another embodiment, however, member 22 is formed from an alloy of: (i) a high density material; and (ii) an alloying agent.

One example of an alloyed material of the present invention for member 22 comprises: (i) a first element selected from the group consisting of gold, platinum, palladium, silver, and tungsten; and (ii) an alloying agent, wherein the alloying agent is a second element which is different from the first element. The combination of the first element and the second element or alloying agent yields combined elements which achieve a desired rigidity and ductility for elongate member 22 to be inserted within and negotiate a root canal of a tooth.

Gold, platinum, and palladium can be employed as alloying agents for each other, such as by combining gold and palladium, for example. Optionally, rhodium, iridium, ruthenium, osmium, copper, chromium, iron, nickel, titanium, silver and tungsten and other materials are examples of materials which are also useful as alloying agents for gold, platinum and/or palladium.

One embodiment of a material used in the present invention to form member 22 comprises an alloy of a high density radiopaque material, such as gold, platinum, palladium, silver, and/or tungsten and a low density material such as stainless steel or nickel-titanium. In another embodiment, the dental tool comprises an alloy of (i) a material such as gold, platinum, palladium and/or tungsten; and (ii) copper, chromium, iron, nickel, silver and/or titanium.

Accordingly, the alloying agent may be selected from the group consisting of copper, chromium, iron, nickel, titanium, gold, platinum, palladium, silver, tungsten, rhodium, iridium, ruthenium, and osmium. However, other alloying agents which combine with the high density material to accomplish the objective of the desired rigidity and ductility of elongate member 22 are also available.

As is apparent from the foregoing discussion, a high density material may serve as an alloying agent for another high density material or an alloying agent may be selected which is not necessarily a high density material. Thus, examples of alloying agents for gold include copper, chromium, iron, nickel, titanium, platinum, palladium, silver, tungsten, rhodium, iridium, osmium and ruthenium; examples of alloying agents for platinum include copper, chromium, iron, nickel, titanium, gold, palladium, silver, tungsten, rhodium, iridium, osmium and ruthenium; examples of alloying agents for palladium include copper, chromium, iron, nickel, titanium, gold, platinum, silver, tungsten, rhodium, iridium, osmium and ruthenium, and so on.

Cost factors may suggest the use of tungsten, palladium or silver, rather than gold or platinum, in certain commercial settings. Examples of alloying agents which are particularly useful in conjunction with tungsten include copper and nickel. Tungsten and other materials described herein as being useful for member 22 may be plated with a material such as gold, palladium or platinum, for example, or with other suitable materials. Although silver is preferably employed in an alloy form, pure silver may be employed for member 22, such as in a disposable embodiment, for example.

An example of an alloyed composition used to form member 22 includes a composition comprising (i) a high density material in the range of about 0.1% by weight to about 99.9% by weight; and (ii) an alloying agent in the range of about 0.1% by weight to about 99.9% by weight. Another example of an alloyed composition includes a composition comprising (i) a high density material in the range of about 5% by weight to about 95% by weight; and (ii) an alloying agent in the range of about 5% by weight to about 95% by weight. Yet another example of an alloyed composition includes (i) a composition comprising (i) a high density material in the range of about 25% by weight to about 75% by weight; and (ii) an alloying agent in the range of about 25% by weight to about 75% by weight.

Optionally, the high density material may be present in the alloy in an amount by weight greater than about 50%, greater than about 75%, or greater than about 90%.

The radiopaque endodontic marking tool is configured for placement within a root canal for detection by a radiographic instrument in order to determine the size of the root canal and to determine if the size of a tool to be used within the root canal is appropriate. Proximal end 26 of elongate member 22 is sheathed within handle 28 such that a portion of radiopaque member 22 extends from a distal stop end 29 of handle 28 with sufficient length to extend into a root canal.

The radiopaque member 22 is preferably substantially straight, and flexible enough to negotiate the angles of the root canal. However, it will be appreciated that radiopaque member 22 may be angled at its proximal end such that the radiopaque member is convenient to manipulate. Optionally, the handle is designed for convenient manipulation of the measuring instrument, such as by being angled.

Figure 3:
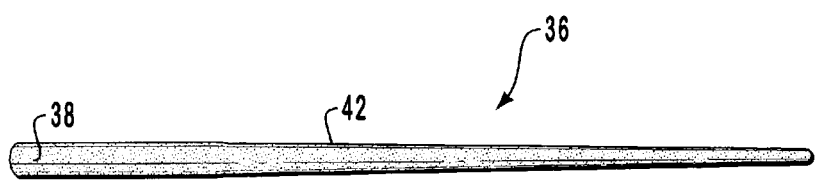
FIG. 3 is a top view of another embodiment of an endodontic marking tool of the present invention.

In one embodiment, such as shown in FIG. 3, elongate member 36 of the present invention has an integral handle 38. Although the surfaces 40, 42 of the elongate members shown in FIGS. 2 and 3 are smooth, optionally, the elongate member of the present invention may be designed to enhance manipulation of the surfaces of a root canal, such as by having cutting flutes, knurls, grooves, notches, or ridges, for example. Before or after the manipulation of root canal surfaces, the position of the instrument within the root canal may be determined through radiography. The endodontic tool of the present invention may be an endodontic file, for instance. By way of example, the endodontic file may be configured in accordance with or similar to the endodontic instruments described in the U.S. Patent Application entitled "Endodontic Systems for Progressively, Sectionally, and Anatomically Preparing Root Canals with Specific Instruments for each Section having Predetermined Working Lengths," filed Jan. 28, 1998, Ser. No. 09/014,762, which is incorporated herein in its entirety by reference.

Fluted files can be frictionally pressed against root canal surfaces in an abrading manner. Before or after such abrasion, the position of the file can be determined through radiography by taking an x-ray, for example. The flutes of the instrument can be aggressive or less aggressive. However, less aggressive flutes may be useful to negotiate tight places within a root canal.

Figure 4:
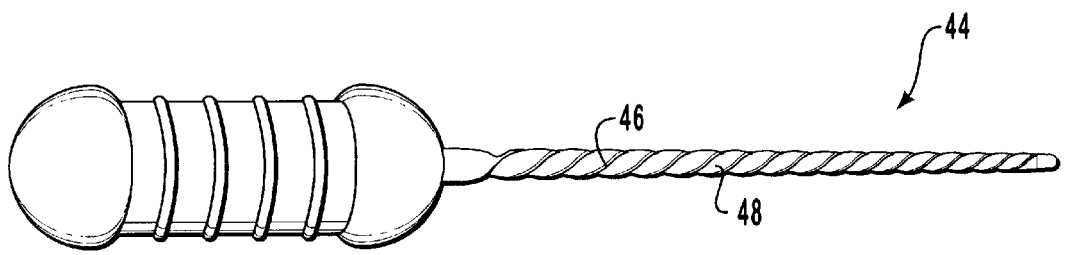
FIG. 4 is a top view of yet another embodiment of an endodontic marking tool of the present invention.

FIG. 4 demonstrates an example of an endodontic file 44 of the present invention having fluting 46 on an elongate member 48 thereof. File 44 has an elongate member 48 which comprises a high density material and, optionally, an alloying agent, as discussed above.

Optionally, the tool of the present invention may comprise a slender rod or wire, a bit, or a variety of other tools which will permit insertion within a root canal and have a high density radiopaque material thereon. Such tools have an elongate member with a distal insertion end opposite a proximal end.

The elongate members (e.g., members 22, 36, 48) disclosed herein are each examples of elongate means for positioning within a root canal of a tooth for radiographic viewing. Each handle disclosed herein (e.g., handles 28 and 38) is an example of a handle means for grasping and moving the elongate means.

The handle may be integrally coupled to the elongate member or nonintegrally coupled thereto. Thus, in one embodiment, the endodontic tool of the present invention comprises (i) an elongate means, e.g., shaft portion 36; and (ii) a handle means, e.g., handle portion 38, for grasping and moving the elongate means. Handle 28 may be coupled integrally to member 22 or nonintegrally coupled thereto.

Figure 5:
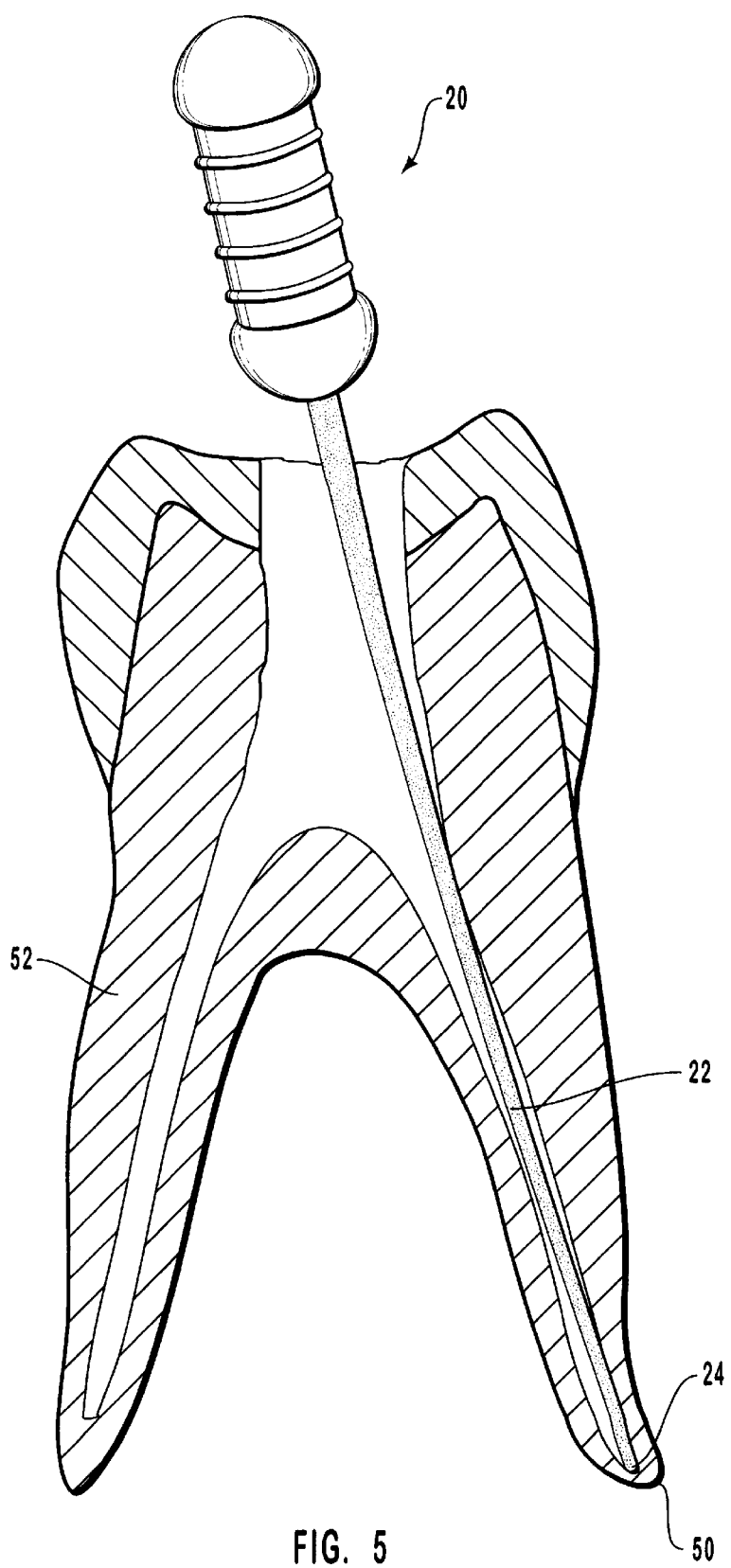
FIG. 5 is a view of a cross section of a tooth which has undergone a root canal procedure and has received the tool of FIG. 2 within a root canal thereof preparatory to radiography of the tooth and tool to determine the distance between the tip of the tool and the apex of the root canal.

FIG. 5 demonstrates an example of the dental tool 20 of FIG. 2 being placed within a root canal of a partially cleaned tooth. As shown, the elongate member 22 of tool 20 is disposed in the root canal. Once a radiograph is taken of the tooth 52 and dental tool 20, it will be possible for the practitioner to determine the distance between the end 24 of dental tool 20 and the apex 50 of tooth 52, thereby determining any distance which the practitioner must further bore or clean.

Figure 1:
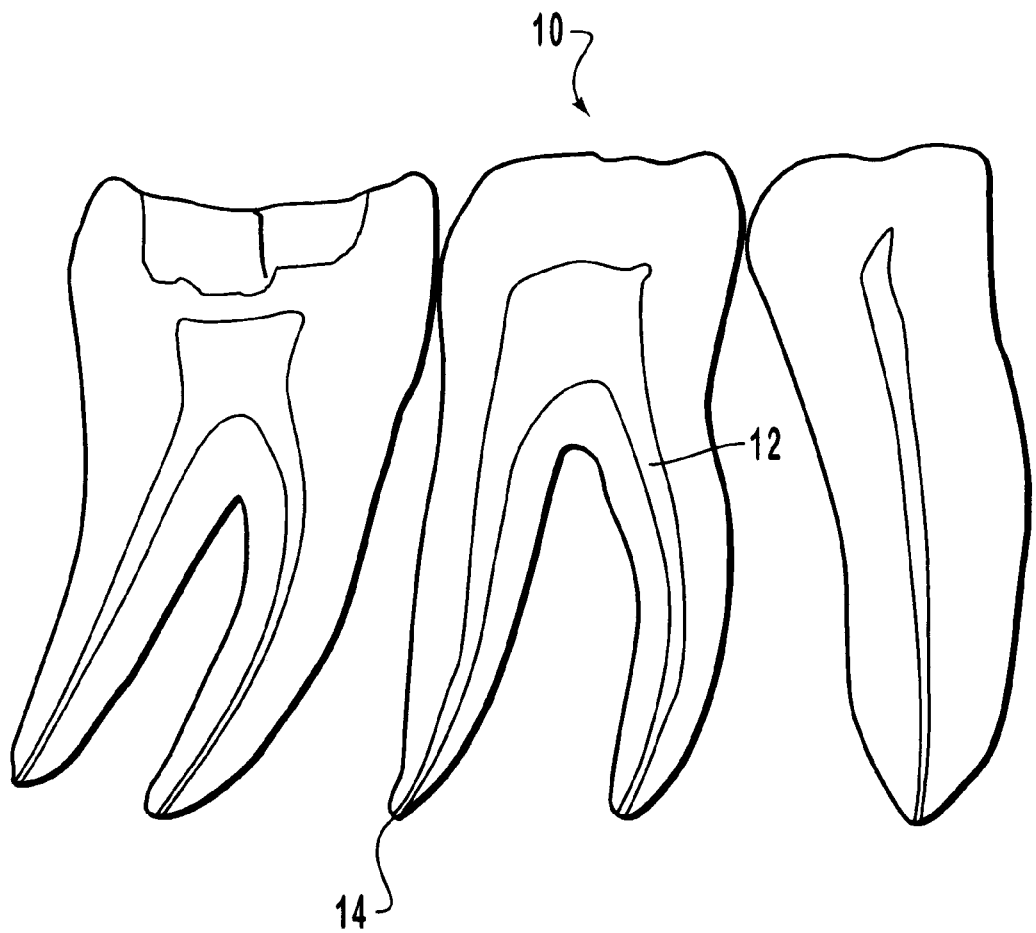
FIG. 1 is a depiction of a preoperative x-ray image of a series of diseased teeth taken in order to make an initial determination of the working length of an endodontic tool.

According to one method of use, an initial radiographic image of a tooth is made and the depth of the root canals of the tooth are estimated, as discussed with respect to FIG. 1. Then the pulp chamber of the tooth is opened. Next, at least a large part of the pulp in the pulp chamber and canals is removed. Elongate member 22 of tool 20 is then placed into the root canal. A radiograph, such as an x-ray is then made of the tooth and tool 20. The distance between the end 24 of dental tool 20 and the apex 50 of the tooth 52 is determined, after which the practitioner can determine if further cleaning is required. However, this is just one potential use of tool 20 and tool 20 may be employed in a variety of different radiographic procedures used to determine the length of a root canal.

With respect to the size of the desired dental tools, the tools can be generally the same diameter and length as files or other tools typically used in endodontic procedures, for example, or other sizes which fit into a root canal and allow negotiation therein. The tools may be tapered such as in the shape of a standard ISO tapered file, for example.

EXAMPLES OF THE INVENTION

As mentioned above, in one embodiment, the high density materials of the present invention are employed in pure amounts, rather than alloys. Examples of such pure materials which are useful for the formation of member 22 include gold, platinum, palladium, tungsten, and silver. Such materials are highly radiopaque and can be formed into elongate members having sufficient rigidity and ductility to extend to a desired location within a root canal of a tooth. The following examples provide hypothetical compositions for forming radiopaque instruments.

Example 1

In this example, an elongate member configured to be inserted within a root canal of a tooth is formed from the following formula:

| Component | Percent by Weight |
|---|---|
| Gold | 100% |

Such a tool would be expected to be highly radiopaque and to have sufficient rigidity and ductility to extend to a desired location within a root canal of a tooth. Gold has a high density, is highly radiopaque, has good corrosion resistance, and is ductile, but is generally high in cost.

Example 2

In this example, an elongate member configured to be inserted within a root canal of a tooth is formed from the following formula:

| Component | Percent by Weight |
|---|---|
| Platinum | 100% |

Such a tool would be expected to be highly radiopaque and to have sufficient rigidity and ductility to extend to a desired location within a root canal of a tooth. Platinum has a high density (and is even slightly higher in density than gold), is highly radiopaque, has good corrosion resistance, is ductile, but is generally high in cost, often costing more than gold.

Example 3

In this example, an elongate member configured to be inserted within a root canal of a tooth is formed from the following formula:

| Component | Percent by Weight |
|---|---|
| Palladium | 100% |

Such a tool would be expected to be highly radiopaque and to have sufficient rigidity and ductility to extend to a desired location within a root canal of a tooth. Palladium has a high density, is highly radiopaque, has good corrosion resistance, and is ductile. Palladium is lower in density than gold, but generally costs less than gold.

Example 4

In this example, an elongate member configured to be inserted within a root canal of a tooth is formed from the following formula:

| Component | Percent by Weight |
|---|---|
| Tungsten | 100% |

Such a tool would be expected to be highly radiopaque and to have sufficient rigidity and ductility to extend to a desired location within a root canal of a tooth. Tungsten has a high density, (and is in fact similar in density to gold), is highly radiopaque, has good corrosion resistance, and is ductile. Tungsten generally costs less than platinum, gold, and palladium.

Example 5

In this example, an elongate member configured to be inserted within a root canal of a tooth is formed from an alloy having the following formula:

| Component | Percent by Weight of the Alloy |
|---|---|
| Gold | 75% |
| Platinum | 25% |

Such an alloyed tool would be expected to be highly radiopaque, to have good corrosion resistance, and to have sufficient rigidity and ductility to extend to a desired location within a root canal of a tooth. Such a tool would also be expected to be generally high in cost.

Example 6

In this example, an elongate member configured to be inserted within a root canal of a tooth is formed from an alloy having the following formula:

| Component | Percent by Weight of the Alloy |
|---|---|
| Platinum | 75% |
| Gold | 25% |

Such an alloyed tool would be expected to be highly radiopaque, to have good corrosion resistance, and to have sufficient rigidity and ductility to extend to a desired location within a root canal of a tooth. Such a tool would also be expected to be generally high in cost.

Example 7

In this example, an elongate member configured to be inserted within a root canal of a tooth is formed from an alloy having the following formula:

| Component | Percent by Weight of the Alloy |
|---|---|
| Palladium | 75% |
| Gold | 25% |

Such an alloyed tool would be expected to be highly radiopaque, to have good corrosion resistance, and to have sufficient rigidity and ductility to extend to a desired location within a root canal of a tooth. Such a tool would also be expected to be relatively low in cost by comparison to the alloyed materials of examples 5 and 6.

Example 8

In this example, an elongate member configured to be inserted within a root canal of a tooth is formed from an alloy having the following formula:

| Component | Percent by Weight of the Alloy |
|---|---|
| Palladium | 75% |
| Platinum | 25% |

Such an alloyed tool would be expected to be highly radiopaque, to have good corrosion resistance, and to have sufficient rigidity and ductility to extend to a desired location within a root canal of a tooth. Such a tool would also be expected to be relatively low in cost by comparison to the alloyed materials of examples 5 and 6.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by united states letters patent is:

1. A radiopaque endodontic tool configured for placement within a root canal for detection by a radiographic instrument, the tool comprising:

elongate means for positioning within a root canal of a tooth for radiographic viewing, the elongate means having a distal insertion end; and
a proximal end; and handle means for grasping and moving the elongate means;

wherein the elongate means comprises a non-toxic, high density, radiopaque, alloy material including (i) palladium; and (ii) an alloying agent selected from the group consisting of copper, chromium iron, nickel, titanium, gold, silver, platinum, tungsten, rhodium, iridium, ruthenium, and osmium;

wherein the elongate means has sufficient rigidity and is sufficiently ductile to extend to a desired location within a root canal of a tooth; and wherein the elongate means has a length and outer diameter that enables the elongate means to be inserted within a root canal of a tooth.

2. An endodontic tool as recited in claim 1, wherein the endodontic tool comprises an endodontic file.

3. An endodontic tool as recited in claim 1, wherein the endodontic tool comprises a wire.

4. An endodontic tool as recited in claim 1, wherein the handle means is integrally coupled to the elongate means.

5. An endodontic tool as recited in claim 1, wherein the handle means is nonintegrally coupled to the elongate means.

6. A radiopaque endodontic tool configured for placement within a root canal for detection by a radiographic instrument, the tool comprising:

an elongate member having a distal insertion end opposite a proximal end;

wherein the elongate member comprises a non-toxic, high density, radiopaque, alloy material including (i) palladium, and (ii) an alloying agent selected from the group consisting of copper, chromium, iron, nickel, titanium gold, silver, platinum, tungsten, rhodium, iridium ruthenium, and osmium;

wherein the elongate member has sufficient rigidity and ductility to extend to a desired location within a root canal of a tooth; and wherein the elongate member has a length and outer diameter that enables the elongate member to be inserted within a root canal of a tooth.

7. An endodontic tool as recited in claim 6, wherein the endodontic tool comprises an endodontic file.

8. An endodontic tool as recited in claim 6, wherein the endodontic tool comprises a wire.

* * * * *

UNITED STATES PATENT AND TRADEMARK OFFICE
CERTIFICATE OF CORRECTION

PATENT NO.     : 6,155,825
DATED          : December 5, 2000
INVENTOR(S)    : Dan E. Fischer; Dan J. Bills Page 1 of 1

It is certified that error appears in the above-identified patent and that said Letters Patent is hereby corrected as shown below:

<u>Column 9,</u>
Line 43, after "secured by" change "united states letters patent" to -- United States Letters Patent --

<u>Column 10,</u>
Line 9, after "consisting of copper" change "chromium" to -- chromium, --
Line 37, before "gold, silver" change "titanium" to -- titanium, --

Signed and Sealed this

Fourth Day of December, 2001

Attest:

*Nicholas P. Godici*

NICHOLAS P. GODICI
*Attesting Officer*      *Acting Director of the United States Patent and Trademark Office*